US005656143A

United States Patent [19]
Swetnam et al.

[11] Patent Number: 5,656,143
[45] Date of Patent: Aug. 12, 1997

[54] SENSORS FOR THE ANALYSIS OF MOLTEN METALS

[75] Inventors: Mark Andrew Swetnam, Beaver Falls, Pa.; Lyn Holt, Witney; Stefan Ryszard Witek, Oxford, both of United Kingdom

[73] Assignee: Cookson Group PLC, London, United Kingdom

[21] Appl. No.: 464,858

[22] PCT Filed: Jan. 11, 1994

[86] PCT No.: PCT/GB94/00045

§ 371 Date: Sep. 21, 1995

§ 102(e) Date: Sep. 21, 1995

[87] PCT Pub. No.: WO94/16318

PCT Pub. Date: Jul. 21, 1994

[30] Foreign Application Priority Data

Jan. 12, 1993 [GB] United Kingdom ............ 9300435

[51] Int. Cl.$^6$ ................................. G01N 27/26
[52] U.S. Cl. .................. 204/421; 204/422; 204/423; 205/786.5; 422/82.01; 422/82.02; 422/82.03; 436/73; 436/79; 436/83
[58] Field of Search ........................ 204/421, 422, 204/423; 205/786.5; 422/82.01, 82.02, 82.03; 436/73, 79, 83

[56] References Cited

U.S. PATENT DOCUMENTS

| | | | |
|---|---|---|---|
| 4,406,754 | 9/1983 | Narita et al. | 204/424 |
| 4,868,142 | 9/1989 | Waisala et al. | 501/85 |
| 4,882,032 | 11/1989 | Tiwari | 204/422 |
| 5,112,456 | 5/1992 | Worrell et al. | 204/422 |
| 5,228,245 | 7/1993 | Rice et al. | 51/319 |

FOREIGN PATENT DOCUMENTS

| | | |
|---|---|---|
| 2330003 | 10/1976 | France . |
| 4320956 | 11/1992 | Japan . |
| 1470558 | 7/1975 | United Kingdom . |
| 1603496 | 11/1981 | United Kingdom . |

OTHER PUBLICATIONS

International Search Report.

"Zirconia–toughened Sodium Beta–Alumina Solid Electrolyte", Journal Of Materials Science, 21 (1986) 4221–4226 no month available.

"Dense Polycrystalline Strontium B"—and B–Alumina: Synthesis, XRD Characterization andThermal Stability, Mat. Res. Bull., vol. 26, pp. 909–916, 1991 no month available.

*Primary Examiner*—Bruce F. Bell
*Attorney, Agent, or Firm*—Sixbey Friedman Leedom & Ferguson; Thomas W. Cole

[57] ABSTRACT

A solid electrolyte sensor to measuring the amount of trace elements, such as sulfur, in molten metals such as steel is provided wherein zirconia toughened strontium β-alumina is used as the solid electrolyte. The resulting sensor is highly resistant to thermal shock, and is suitable for use with molten metals at temperatures of 1350° C. or higher.

7 Claims, 2 Drawing Sheets

SENSORS FOR THE ANALYSIS OF MOLTEN METALS

BACKGROUND OF THE INVENTION

This application is a 371 of PCT/GB94/00045 filed Jun. 11, 1994.

The present invention relates to sensors for the analysis of molten metals and, in particular, to sensors for the measurement of trace elements, such as sulfur, in steel making processes.

Solid electrolyte sensors are based upon the principle that an electric potential difference (voltage) exists across an electrolyte which contains a mobile ion of a given chemical element and which separates two compartments in which the same element has different chemical activities.

The voltage is related to the two chemical activities via the so-called Nernst equation:

$$E = -\frac{RT}{zF} \ln \frac{a_{melt}}{a_{reference}}$$

where
R=the molar gas constant (8.3144 Joule/mole Kelvin);
T=the absolute temperature in Kelvin;
z=the number of electrons transferred in the electromechanical equilibrium under consideration—this is a known value for each system;
F=Faraday's constant (96.485 Coulomb/mole)
and $a_{melt}$ and $a_{reference}$ are the two chemical activities.

One of the two chemical activities is fixed by employing a well-known and well-defined chemical system, a so-called reference system, on one side of the electrolyte. Provided the temperature of the two electrolyte interfaces is known (and the same for both interfaces), the voltage across the electrolyte can be directly related to the unknown chemical activity. This chemical activity in turn can be related to the concentration of the element.

Sensors based upon stabilised zirconia solid electrolytes are routinely used in the steel and copper industries to measure the concentration of oxygen in the molten metals. At the present time, the most widely used sensor for molten steel is the so-called "Celox" probe made by Electro-Nite which is a dip-sensor engineered to have a very short lifetime of about one minute in molten steel. The end of the sensor which is dipped into the molten steel comprises a dense cardboard tube with a ceramic and in which the sensor electrolyte is mounted.

GB-A-2196430 describes a continuous sensor for molten steel in which a heat buffer of a refractory material is incorporated between an inner tube of a refractory material in which the measuring element is mounted, and an outer tube which surrounds the inner tube at least over the sensor portion which is to be dipped into the molten metal. The refractory material prevents large temperature variations of the measuring element and thus also prevents large temperature differentials between the portion of the measuring element dipped into the molten metal and the portion of the measuring element above the molten metal.

Various electrochemical sensors for other elements in molten metals are undergoing development and include aluminium in steel and zinc, silicon in steel and pig iron, sulfur in pig iron and copper, phosphorus in pig iron and copper, chromium in steel, sodium in aluminium, copper in copper-tin, calcium in lead-calcium and lithium in aliminium-lithium. The main obstacle in the development of such devices is engineering a device that can withstand both the high temperature involved and the chemically aggressive environments.

For example, GB-A-1470558 uses as the solid electrolyte sodium β-alumina the electrolyte conducting by the movement of sodium ions through the matrix. Although sodium β-alumina is chemically a suitable solid electrolyte for the measurement of sulfur for example in iron or steel, because the sodium ions react with the sulfur ions in the steel to form sodium sulfide according to the equation:

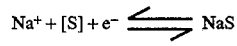

in practice, sensors constructed using sodium β-alumina as the solid electrolyte suffer from severe thermal shock when immersed, for example, in molten steel and will thus break in use. The β-alumina of lithium, potassium, rubidium, copper, silver, thallium and gallium are also disclosed for use in this prior art method and apparatus.

SUMMARY OF THE INVENTION

We have now developed a sensor for the analysis of molten metals which is based upon a modified strontium β-alumina which has significantly improved thermal shock properties.

Accordingly, the present invention provides a sensor for the measurement of trace elements in molten metals or alloys, which comprises as the solid electrolyte zirconia toughened strontium β-alumina.

The thermal shock resistance of the strontium β-alumina is considerably improved, in accordance with the present invention, by toughening these materials with zirconia. Sensor failure due to thermal shock is thus virtually eliminated. Furthermore, the addition of zirconia to the strontium β-alumina allows materials of high density to be produced because the zirconia acts as a sinter aid during the formation of the materials. The performance of the material as a solid electrolyte relies upon it being of a high density.

The amount of zirconia which is incorporated into the zirconia toughened materials used in the present invention is generally in the range of from 5 to 25% by weight, more preferable from 10 to 20% by weight.

The zirconia toughened strontium β-alumina may be prepared from mixtures of alumina, strontium carbonate and unstabilized zirconia together with small amounts of any desired additives, such as magnesium carbonate (to stabilize the strontium β-alumina structure). The appropriate powder mixture is ball milled in a solvent to a small particle size and then calcined to pre-form the β-alumina phase. The calcined material is then re-milled, and a small quantity of organic binder added. The resulting powder is then isostatically pressed and sintered at high temperatures, for example in the range of from 1600° C. to 1700° C. to produce dense ceramic bodies. The toughening of the materials occurs during the sintering step. As the β-alumina is cooled from the sintering temperature the zirconia changes from the tetragonal form to the monoclinic form which involves a volume increase of about 4%. Stresses are produced in the surrounding matrix of β-alumina and a series of microcracks are formed throughout the ceramic body. The microcracks improve the toughness of the material by absorbing the stresses created in the material when it is subjected to a rapid and very large temperature change. Whilst the strength of the material may be decreased slightly by the zirconia toughening, the toughness of the materials is often increased by over 100%.

The sensor of the present invention is preferably used in combination with an alumina-graphite, a castable refractory or sialon sheath which surrounds the sensor and enables the sensor to be submerged into molten metals, such as molten iron or steel, for extended periods of time. The alumina-graphite, castable refractory and sialon all have excellent refractory properties and are virtually immune to thermal shock. This arrangement enables the sensor to be plunged into the molten metal without the need for any pre-heating.

It will be understood by those skilled in the art that the sensor of the present invention will generally be used with a reference material which ensures that the activity of the chemical species which is being sensed by the sensor remains constant on one side of the solid electrolyte material. For example, when the sensor of the present invention is intended to act as a sensor for sulfur, the reference material may comprise a mixture of molybdenum metal and molybdenum sulfide powders which provides a fixed sulfur partial pressure against which the activity of the sulfur in the molten metal is measured.

The sensor of the present invention is used in combination with a counter electrode which provides an electrically conductive path from the measurement apparatus to the molten metal. It is quite difficult to achieve this for long periods of time as even refractory metals such as molybdenum rapidly dissolve away at high temperatures, for example at the temperature of molten iron. In order to overcome this problem a cermet is used, for example a molybdenum/zirconia composite material which has a good resistance to dissolving an iron, whilst providing a good electrical contact with the melt. For example, a small cup of the cermet material packed with molybdenum powder may be placed in the molten metal. A molybdenum wire is then inserted into the powder to give a good contact.

At elevated temperatures, the mobile strontium ions within the ceramic electrolyte are able to move freely through the electrolyte. On the inside of the cell is an appropriate reference material. For a sulfur sensor, a mixture of molybdenum metal and molybdenum sulfide powders may be used. This combination fulfils all of the requirements for a good reference material, i.e. it provides a good electrical contact with the cell and the wire, it is stable at high temperatures such as steelmaking temperatures, and it provides a suitable sulfur partial pressure to act as a reference point in the cell. For strontium β-alumina, the moving strontium ions react to form strontium sulfide on the inside wall of the electrolyte. Because the sulfur partial pressure is fixed and known, the strontium activity on the reference side of the electrolyte is now fixed and known. At the same time, the outer surface of the electrolyte is in contact with the molten metal which has an unknown sulfur activity. The strontium ions react with the sulfur in the metal to form strontium sulfide on the outer surface of the solid electrolyte cup. The strontium activity on the melt side of the electrolyte is now fixed by the sulfur activity in the melt. Since the electrolyte is a good conductor of strontium ions, the difference in strontium activity on both sides leads to movement of the ions (from high to low activity), which alters the chemical equilibria on both sides in opposite directions, and leads to a charge imbalance across the electrolyte. The charge imbalance counteracts the movement of the ions, and an equilibrium is reached. The charge imbalance can be measured as an electric potential difference between the two sides of the electrolyte, and the relationship between this potential difference E, the two sulfur activities and the absolute temperature T is described by the Nernst equation given above.

The points between which the potential differences is measured are the sensor reference material and the molten metal.

For the measurement of sulfur in molten iron in order to be able to calculate accurately the sulfur concentration from the measured sulfur activity, the carbon and silicon concentrations of the melt must be input into the equation as these also affect the sulfur activity. These values are readily available from the blast furnace operation.

BRIEF DESCRIPTION OF THE DRAWINGS

The present invention will be further described with reference to the Figures of the accompanying drawings in which.

DETAILED DESCRIPTION OF THE PREFERRED EMBODIMENT

Figure 1:
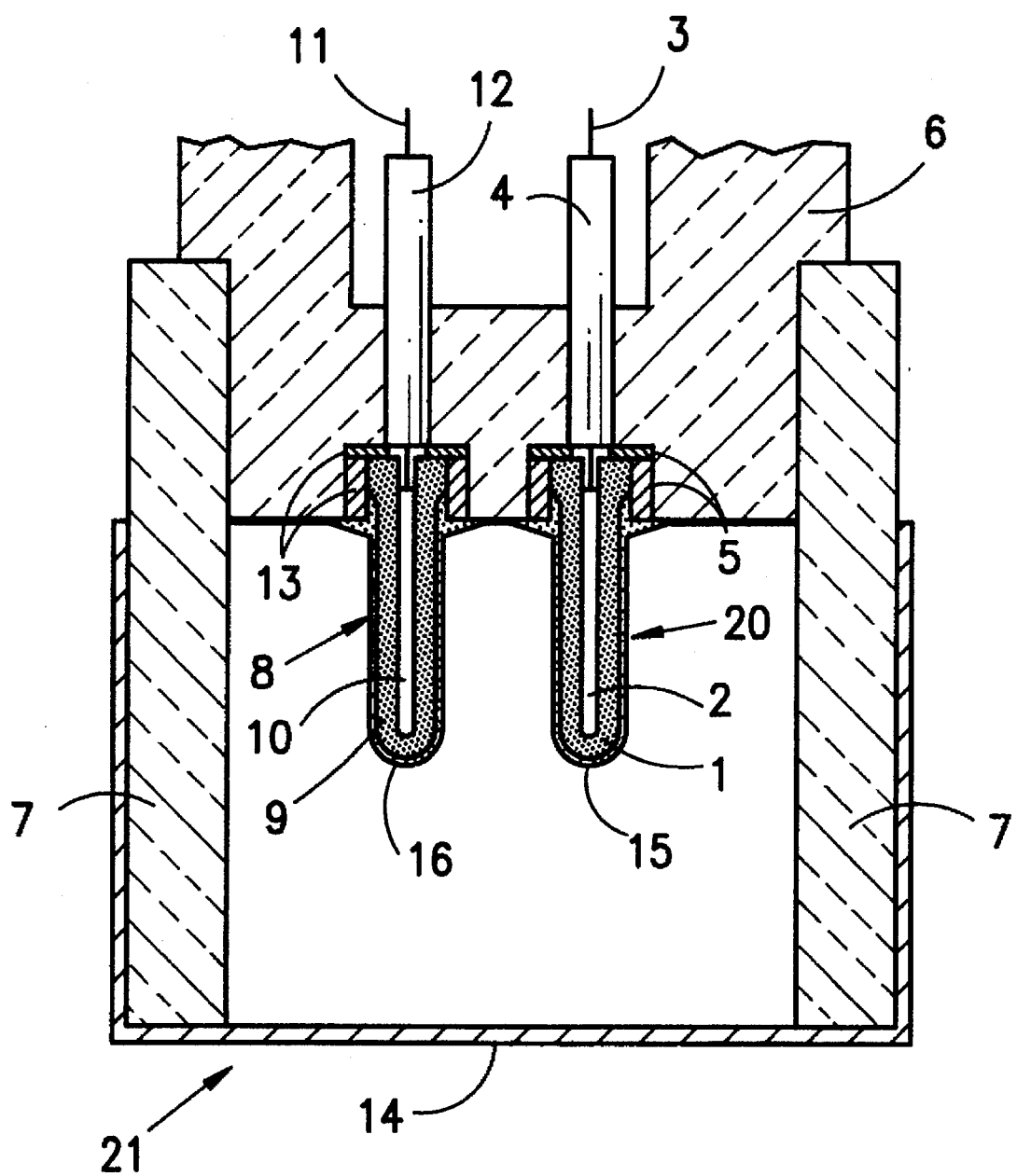
FIG. 1 illustrates a probe for the measurement of sulfur which includes therein a sensor in accordance with the present invention.

Referring to FIG. 1 of the drawings the sensor 20 comprises as the solid electrolyte 1 a zirconia toughened strontium β-alumina. The solid electrolyte 1 is in the form of a ceramic cup which surrounds a reference material 2 comprising a mixture of molybdenum/molybdenum sulfide. The reference material 2 provides the fixed sulfur partial pressure against which the activity of the sulfur in the molten metal into which the sensor is to be dipped is measured. A molybdenum wire 3 extends through an alumina tube 4 and an alumina washer 5 into the reference powder 2. The sensor is housed in an alumina-graphite sheath 6 which surrounds the upper portion of the sensor and through which the tube 4 and washer 5 are inserted. The alumina graphite sheath 6 is connected to an alumina graphite shroud 7 which surrounds both the sensor 20 and a counter electrode 8 to form the tip of the probe. The counter electrode 8 comprises a cermet cup 9 which surrounds molybdenum powder 10 into which a molybdenum wire 11 extends. The molybdenum wire 11 extends through an alumina tube 12 and alumina washer 13. The counter electrode 8 provides an electrically conducting path from the measurement apparatus to the molten metal. The cermet 9 is a molybdenum/zirconia composite that displays a good resistance to dissolving in molten metals, whilst providing good electrical contact.

The sulfur probe has a metal cap 14 placed over the tip thereof and surrounding the alumina graphite shroud 7. This metal cap melts away after a few seconds immersion in the molten metal. The sensor 20 and counter electrode 8 both have metal caps 15 and 16 which surround the solid electrolyte 1 and cermet 9, respectively. The metal caps 15 and 16 help to prevent the ceramic materials suffering from thermal shock and melt away after a few seconds immersion in the molten metal.

The tip only of the sulfur probe 21 is depicted in the Figure of the drawings. The sulfur probe 21 is attached to a re-usable device through which connections are made from the molybdenum wires 3 and 11 to a control box for effecting the appropriate measurements.

The present invention will be further described with reference to the following Example.

EXAMPLE 1

The probe design as shown in FIG. 1 was used to determine the level of sulphur in molten iron.

Figure 2:
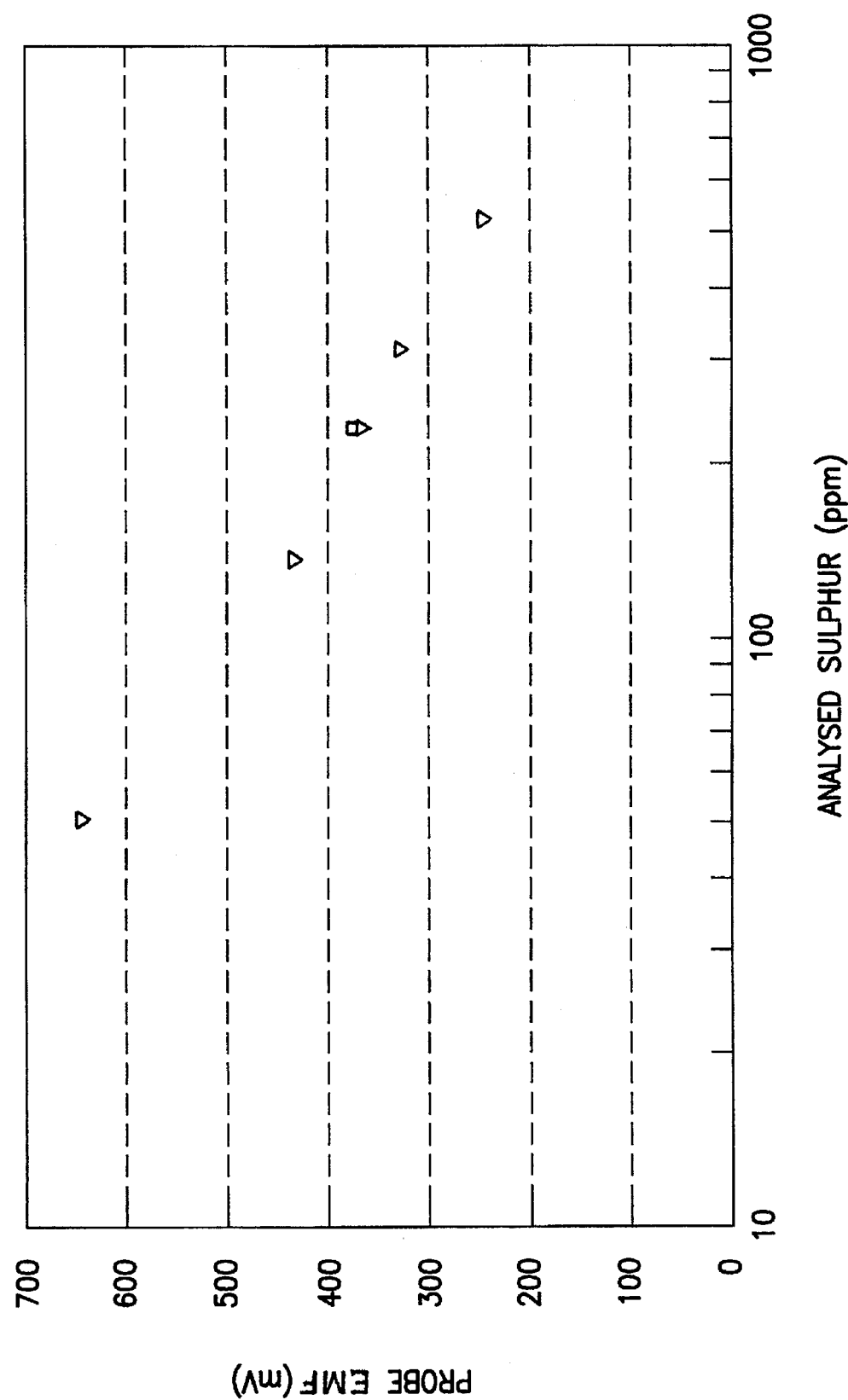
FIG. 2 is a graph of the analysed sulphur (ppm) versus the probe EMF values obtained measuring the sulphur content of molten iron.

The trials were carried out in two steel plants, in vessels containing up to 300 tons of molten iron. The results were obtained with several probes. The probes were immersed in the iron which was at approximately 1350° C., before and after desulphurisation with magnesium. Samples were taken from the melt for each probe and analysed using a LECO analyzer, and these values are plotted against the probe EMF values in the graph in FIG. 2. A log-linear relationship is observed as predicted by the Nernst equation.

The data plotted in the graph is tabulated below:

| Probe EMF (mV) | Analysed Sulphur (ppm) |
|---|---|
| 240 | 620 |
| 320 | 310 |
| 320 | 310 |
| 360 | 230 |
| 370 | 230 |
| 430 | 240 |
| 640 | 50 |

We claim:

1. A high temperature electrolytic sensor for the measurement of trace elements in molten metals or alloys, which comprises a solid electrolyte formed from zirconia toughened strontium β-alumina for both rendering the sensor operable at temperatures on the order of 1350° C. and for enhancing the thermal shock properties of the sensor.

2. A sensor as claimed in claim 1 wherein the zirconia toughened strontium β-alumina comprises 5 to 25% by weight zirconia.

3. A sensor as claimed in claim 2 wherein the zirconia toughened strontium β-alumina comprises 10 to 20% by weight zirconia.

4. A sensor as claimed in claim 1 wherein the sensor is surrounded by an alumina graphite, cast refractory or sialon sheath.

5. A sensor as claimed in claim 1 wherein the solid electrolyte material is in contact with a reference material which ensures that the activity of the chemical species which is to be sensed by the sensor remains constant on one side of the solid electrolyte material.

6. A sensor as claimed in claim 5 which is a sensor for the measurement of sulfur ions in a molten metal and the reference material comprises a mixture of molybdenum and molybdenum sulfide.

7. A sensor as claimed in claim 1 which is used in combination with a counter electrode which provides an electrically conductive path from a measurement apparatus to the molten metal.

* * * * *